(12) United States Patent
Barron

(10) Patent No.: US 8,518,435 B2
(45) Date of Patent: Aug. 27, 2013

(54) **HOMEOPATHIC FORMULATION CONSISTING OF *BRYONIA ALBA* AND *PULSATILLA* SPP**

(76) Inventor: Jon Barron, Chatsworth, CA (US)

( * ) Notice: Subject to any disclaimer, the term of this patent is extended or adjusted under 35 U.S.C. 154(b) by 0 days.

(21) Appl. No.: 13/530,407

(22) Filed: Jun. 22, 2012

(65) Prior Publication Data

US 2013/0004591 A1    Jan. 3, 2013

Related U.S. Application Data

(60) Provisional application No. 61/502,208, filed on Jun. 28, 2011.

(51) Int. Cl.
*A61K 47/06* (2006.01)

(52) U.S. Cl.
USPC .......................................................... 424/439

(58) Field of Classification Search
None
See application file for complete search history.

(56) References Cited

U.S. PATENT DOCUMENTS 7,919,127 B2 * 4/2011 Choi et al. .................... 424/773

OTHER PUBLICATIONS

Barak, V., et al., The Effect of Herbal Remedies on the Production of Human Inflammatory and Anti-inflammatory Cytokines, Isr. Med. Assoc. J. (2002) 4(Suppl):919-922.
Barak, V., et al., The effect of Sambucol, a black elderberry-based, natural product, on the production of human cytokines: I. Inflammatory cytokines, Eur. Cytokine Netw. (2001) 12(2):290-296.
Boivin., et al., Multiplex Real-Time PCR Assay for Detection of Influenza and Human Respiratory Syncytial Viruses, J. Clin. Microbiol. (2004) 42(1):45-51.
Bragg, P.C., et al., Apple Cider Vinegar, 58th Ed. (2010) pp. 17-18 (Health Science: Santa Barbara, California).
Chrubasik, S., et al., Zingiberis rhizoma: a comprehensive review on the ginger effect and efficacy profiles, Phytomed. (2005) 12(9):684-701 (Abstract Only).
Denyer, C.V., et al., Isolation of antirhinoviral sesquiterpenes from ginger (Zingiber officinale), J. Nat. Prod. (1994) 57 (5):658-662 (Abstract Only).
Dewey, W.A., Homeopathy in Influenza—a Chorus of Fifty in Harmony, The Journal of the American Institute of Homeopathy, May 1921, pp. 1308-1043.
Dorman, H.J., et al., Antimicrobial agents from plants: antibacterial activity of plant volatile oils, J. Appl. Microbiol. (2000) 88(2):308-16 (Abstract Only).

Eja, M.E., et al., A comparative assessment of the antimicrobial effects of garlic (*Allium sativum*) and antibiotics on diarrheagenic organisms, Southeast Asian J. Trop. Med. Public Health (2007) 38(2):343-8 (Abstract Only).
Gupta, R., et al., Anti-tuberculosis activity of selected medicinal plants against multi-drug resistant *Mycobacterium tuberculosis* isolates, Indian J. Med. Res. (Jun. 2010) 131:809-13 (Abstract Only).
Imanishi, N., et al., Macrophage-mediated inhibitory effect of *Zingiber officinale* Rosc, a traditional oriental herbal medicine, on the growth of influenza A/Aichi/2/68 virus, Am. J. Chin. Med. (2006) 34(1):157-69 (Abstract Only).
Johnson, B., et al., The Antiseptic and Detoxifying Action of Zinc Peroxide on Certain Surgical Aerobic, Anaerobic and Micro-Aerophilic Bacteria, Annals of Surgery (1939) 109(6): 881-911.
Johnston, N., Garlic: A natural antibiotic (Apr. 2002) 5(4):12.
Lamson, D., et al., MassTag Polymerase-Chain-Reaction Detection of Respiratory Pathogens, Including a New Rhinovirus Genotype, That Caused Influenza-Like Illness in New York State during 2004-2005, J. Infect. Dis. (2006) 194:1398-1402.
Roxas, M., et al., Colds and Influenza: A Review of Diagnosis and Conventional, Botanical, and Nutritional Considerations, Alt. Medicine Rev. (2007) 12(1):25-48.
Tzelepis, F., et al., Modulation of CD4+ T Cell-Dependent Specific Cytotoxic CD8+ T Cells Differentiation and Proliferation by the Timing of Increase in the Pathogen Load, PLos ONE (2007) 2(4):e393.
Utsunomiya, T., et al., Glycyrrhizin, an Active Component of Licorice Roots, Reduces Morbidity and Mortality of Mice Infected with Lethal Doses of Influenza Virus, Antimicrob. Agents Chemother. (1997) 41(3):551-556.
Watzinger, F. et al., Real-Time Quantitative PCR Assays for Detection and Monitoring of Pathogenic Human Viruses in Immunosuppressed Pediatric Patients, J. Clin. Microbiol. (2004) 42(11): 5189-5198.
Weber, N.D., et al., In vitro virucidal effects of *Allium sativum* (garlic) extract and compounds, Planta Med. (1992) 58 (5):417-423 (Abstract Only).
Zakay-Rones, Z., et al., Randomized Study of the Efficacy and Safety of Oral Elderberry Extract in the Treatment of Influenza A and B Virus Infections, The Journal of International Medical Research (2004) 32(2):132-40.

* cited by examiner

*Primary Examiner* — Carlos Azpuru
(74) *Attorney, Agent, or Firm* — Amin Talati, LLC; George M. Carrera, Jr.; Janine A. Moderson

(57) ABSTRACT

A nutritional composition or functional food composition is provided comprising homeopathic ingredients for relieving the symptoms of colds and/or flus, in combination with traditional herbal and nutraceutical ingredients, and are efficacious as antipathogens. The formulation includes ingredients balanced in a synergistic manner to elicit complementary effects which both reduce the symptoms of colds and/or flus and provide the potential to reduce pathogenic loads in the body. Methods of making both the core medicinal formulation and suitable dietary supplement and/or functional food embodiments based on the formulation are provided.

10 Claims, No Drawings

HOMEOPATHIC FORMULATION CONSISTING OF *BRYONIA ALBA* AND *PULSATILLA* SPP

This application claims the benefit of earlier filed U.S. Provisional Application No. 61/502,208, filed on Jun. 28, 2011, which is hereby incorporated by reference herein.

FIELD OF THE INVENTION

A nutraceutical formula and functional food composition includes homeopathic ingredients for relieving the symptoms of colds and/or flus, in combination with traditional herbal and nutraceutical ingredients, and are efficacious as antipathogens. The formulation includes ingredients balanced in a synergistic manner to elicit complementary effects which both reduce the symptoms of colds and/or flus and provide the potential to reduce pathogenic loads in the body. Methods of making both the core medicinal formulation and suitable dietary supplement and/or functional food embodiments based on the formulation are described.

BACKGROUND

Homeopathy is a form of alternative medicine in which practitioners treat patients using highly diluted preparations that causes the body to experience low level manifestations of the symptoms that it is trying to eliminate. In homeopathy, this is known as the "law of similars." In a sense, it is not unlike the principle behind vaccination—where the vaccine triggers low level versions of the disease one is trying to prevent, thereby training the immune system to respond to the real disease state if and when it may arise. Homeopathic remedies do not have any direct effect on bacteria or viruses. However, it is believed that they modify the body's response to them by enabling the body's defense mechanism to better recognize certain pathogens to be fought off. Because of their long standing use in the United States, the U.S. Congress passed a law in 1938 declaring that homeopathic remedies are to be regulated by the FDA in the same manner as nonprescription, over-the-counter (OTC) drugs. Thus, homeopathic remedies are required to meet certain legal standards for strength, quality, purity, and packaging.

Homeopathic ingredients can be used to treat coughs, bronchitis, pneumonia, overall weakness, headache, and deep muscle ache, for example. Other remedies are used to treat diseases accompanied by a greenish-yellow discharge, and are prescribed for colds, sinusitis, coughs accompanied by thick phlegm, and can also help with thick nasal congestion. Still other homeopathic remedies made from onions are commonly used to relieve the symptoms of hay fever, nasal congestion, or similar complaints. Such remedies may be obtained from a pharmacy that carries a range of homeopathic medicines.

Traditional medicine (also known as indigenous medicine) comprises medical or medicinal knowledge systems that have developed over generations within various societies before the era of modern medicine. Practices known as traditional medicines include herbal, Ayurveda, Siddha medicine, Unani, ancient Iranian medicine, Islamic medicine, traditional Chinese medicine, traditional Korean medicine, acupuncture, Muti, Ifá, traditional African medicine, and other medical knowledge and practices all over the globe. These and other knowledge systems are actively being studied in branches of science such as ethnopharmacology and ethnobotany. Although traditional medicine has no legal standing in the United States, it is nevertheless global in application, particularly in the Far East, where it has been estimated that up to 80% of the population continues to use these traditional methods to treat primary medical problems. In the past decade or so, research has been increasingly focused on scientific evaluation of traditional medicines and drugs of plant and herbal origin, including methods derived from indigenous or tribal populations. Thus, traditional medicines can include many well-known herbs and spices.

If a way could be found to use herbal and/or nutraceutical ingredients in combination with homeopathic ingredients, balanced in a synergistic manner to elicit complementary effects which both reduce the symptoms of colds and/or flus and provide the potential to reduce pathogenic loads in the body, this would represent a useful contribution to medical and nutritional science.

SUMMARY

One embodiment relates to a liquid medicinal formulation for reducing the symptoms of colds and/or flu that contains several homeopathic ingredients such as *Bryonia alba*, *Pulsatilla*, and *Allium cepa*, and liquid pressings or extracts of traditional and/or nutraceutical ingredients selected from ginger, garlic, onion, olive leaf, habanero, horseradish, liquid ionic zinc, oil of wild mountain oregano, or Apple-Cider Vinegar ("ACV"). The formulation can comprise a nutritional composition or a dietary supplement composition.

Also provided is a method for delivering a liquid medicinal formulation for reducing the symptoms of colds and/or flu in the form of single-dose, functional foods such as, for example, blended with fruit juice or vegetable juice in 2-8 ounce cans or bottles. The liquid medicinal formulation can also comprise a nutritional composition or a dietary supplement composition and may be in the form of a syrup, solution, or suspension.

DETAILED DESCRIPTION

In one aspect, a nutraceutical formulation or composition and/or a functional food composition can include homeopathic ingredients to relieve the symptoms of colds and/or flus, in combination with traditional herbal and nutraceutical ingredients, which also may be efficacious as antipathogens. Certain homeopathic ingredients as described herein have a body of research supporting their efficacy as antipathogens. Embodiments of the formulation include ingredients balanced in a synergistic manner to elicit complementary effects which both reduce the symptoms of colds and/or flus and provide the potential to reduce pathogenic loads in the body. Methods of making both the core medicinal formulation and suitable dietary supplement and/or functional food embodiments based on the formulation are described herein.

Possible homeopathic ingredients for use in various embodiments may include, among others, the following.

*Bryonia alba* is used in homeopathic remedies to treat coughs, bronchitis, pneumonia, overall weakness, headache, and deep muscle ache.

*Pulsatilla* remedies are used to treat diseases accompanied by a greenish-yellow discharge. It is prescribed for colds, sinusitis, coughs accompanied by thick phlegm, and can also help with thick nasal congestion. The genus *Pulsatilla* contains about 33 species of herbaceous perennials native to meadows and prairies of North America, Europe, and Asia.

*Allium cepa* is a homeopathic remedy made from onions that is commonly used to relieve the symptoms of hay fever, nasal congestion, or other similar complaints. It is a popular remedy, and can be obtained from a pharmacy that carries a range of homeopathic medicines.

Examples of traditional medicines that can be used in cold and/or flu formulations include various herbal ingredients, such as, but not limited to the following ingredients.

Garlic is one of the best known infection fighters available for both bacterial and viral infections. It is a natural antibiotic that does not appear to create resistant bacterial and viral strains. In addition, fresh garlic extract has been shown to be virucidal to many viruses (*Planta Med.* (1992) 58(5):417-23). It destroys and/or inhibits various bacteria (*MDD Diagnostics.* (April 2002) Vol. 5, No. 4, p 12) and fungi. Garlic is approximately 1% as potent as penicillin in its antibiotic properties, but can be used at much higher dose levels than penicillin. Garlic is effective against *Streptococcus* (strep), *Staphylococcus* (staph), and even anthrax bacteria (*Southeast Asian J. Trop. Med. Public Health* (2007) 38(2):343-8).

Onion. Onions and garlic share many of the same powerful sulfur bearing compounds that work so effectively as antiviral and antibacterial agents. (*Indian J. Med Res.* (June 2010) 131:809-13).

Ginger traditionally has been used to treat colds and flu. Chinese studies have shown that ginger helps kill influenza viruses (even avian flu) (*Am. J. Chin. Med.* (2006) 34(1):157-69). Ginger has been found to possess antiviral and antimicrobial activities in vitro (*Phytomed.* (2005) 12(9):684-701). For example, one active sesquiterpene isolated from *Zinziber officinale*, beta-sesquiphellandrone, was found to have an $IC_{50}$ of 0.44 µM vs. rhinovirus IB (*J. Nat. Prod.* (1994) 57(5): 658-662).

Olive leaf extract has a long history of being used against illnesses in which microorganisms play a major role. In more recent years, a drug company discovered that in vitro (in a test tube), an extract from olive leaf (calcium elenolate) was effective in eliminating a very broad range of organisms, including bacteria, viruses, parasites, and yeast/mold/fungus. (*Alternative Medicine Review* (2007) 12(1):25-48).

Habañero and Horseradish are stimulants that quicken and excite the body. They energize the body, helping it to marshal its defenses against invading viruses. In addition, these ingredients help to carry blood to all parts of the body. They are also diaphoretics and thus help raise the temperature of the body, which increases the activity of the body's immune system. In vitro, the volatile oils in horseradish have been shown to possess antibiotic properties, which may account for its effectiveness in treating throat and upper respiratory tract infections (*Arch. Hyg. Bakteriol.* (1957) 141(3):182-97).

Like colloidal silver, liquid zinc (or liquid ionic zinc) possesses both antibacterial and antiviral properties, but without the potential toxicity issues found with silver. Zinc is found in all body fluids, including the moisture in the eyes, lungs, nose, urine, and saliva. Proper zinc levels offer a defense against the entrance of pathogens. In the 1800's, surgeons used zinc as an antiseptic/antibiotic after surgery, after they noted its healing properties. Wounds would heal, at times, as quickly as 24 hours after an operation, without swelling, and scarring was barely noticeable after a short period of time. See, for example, *Annals of Surgery* (1939) Vol. 109, No. 6, 881-911. A useful liquid zinc supplement is available from Angstrom Minerals (Fillmore, Utah).

Numerous studies have shown wild mountain ("WM") oregano oil (not to be confused with the oregano found in a home kitchen) to be a potent antimicrobial ingredient. It has been proven useful as an antiviral, antibacterial, and antifungal agent, rivaling even pharmaceutical antibiotics such as streptomycin, penicillin, vancomycin, nystatin, and amphotericin in its ability to eliminate microbes (*J. Appl. Microbiol.* (2000) 88(2):308-16). Remarkably, WM oregano oil acts without promoting the development of drug resistant strains and other problems often attributed to the use of standard antibiotics. In addition to this already impressive list of abilities oregano oil is also a powerful parasitic expellant.

Apple-Cider Vinegar ("ACV") is effective against a number of different types of germs that attack the throat. In effect, it can act like a sponge and draws out throat germs and toxins from the surrounding tissue. ACV also stimulates a condition called acetolysis in which toxic wastes that are harmful to the body are broken down and rendered harmless. (Paul Bragg and Patricia Bragg, Apple Cider Vinegar, Miracle Health System, pp. 17-18 (Health Science, Santa Barbara, Calif., 2010). ACV is commercially available from Bragg Live Foods, Inc. (Santa Barbara, Calif.).

In another embodiment, a nutritional composition comprising a complementary combination of homeopathic and traditional medicine components or ingredients has been discovered. Use of the components singularly does not produce the desired effects of relief from the symptoms of colds and/or flu. The advantageous effects can be achieved by combining the ingredients in a multi-component formula. If fact, the multi-component combination, in its various embodiments as described herein, is essential to its functionality. Single component remedies, including one or more components administered individually or serially, with or without certain antibacterial and antiviral drugs, do not achieve this effect.

Antibiotic resistance to man-made drugs is almost impossible to prevent since it is the result of some simple rules of natural selection. Any population of organisms, bacteria included, naturally includes genetic variants with unusual traits such as the ability to withstand a particular antibiotic's attack. When said antibiotic is used and kills a particular sub-group of defenseless bacteria, it leaves behind those bacteria that can resist it. These antibiotic-resistant bacterial variants then multiply, increasing their numbers a million fold in a single day, instantly becoming the dominant variant. In other words, the very act of using an antibiotic creates the opportunity for strains resistant to it to flourish.

Unfortunately, because each antibiotic compound or antiviral compound is a single compound and generally one dimensional or limited in its effects, in that most chemical agents have one preferred mechanism of action, it's not that hard for microbes to "evolve" around such attacks. For example, microbes resistant to penicillin have developed cell walls or cell wall coats different from the norm that prevent the penicillin from binding. Similarly, other microbe variants prevent antibiotics from binding to ribosomes, thus neutralizing the effect of those antibiotics.

Because of their primitive structure, viruses may mutate even more easily than bacteria. Whereas antibiotics can remain effective for 2-5 years before resistant strains render them ineffective, antiviral resistant strains can appear in a matter of months, or even weeks. In fact, this resistance has been observed with oseltamivir. Although governments began stockpiling it as a safety net for avian flu and swine flu, both types of flu arrived on the scene displaying resistance to oseltamivir and the other antivirals during the years of the widespread pandemics. Further, even susceptible flu strains that oseltamivir successfully treated in the past are developing resistant strains by the month.

The embodiments described herein can avoid this problem of drug resistance by making use of the multi-dimensional defenses afforded by natural substances and geometrically enhancing the beneficial effects, partly by incorporating multiple natural or herbal substances. While pathogens can quickly "evolve around" antibiotic and antiviral drugs; they are unable to do so against most natural antipathogens such as garlic, olive leaf, and oil of oregano even given tens of thousands of years to do so. How does this happen?

Natural antipathogens are multi-dimensional. They often contain dozens, if not hundreds, of pharmacologically and physiologically significant biochemicals. Not all of them are "active" (in a drug, dose-response relationship) but many of the so called "non-active" (or uninvestigated) biochemicals work to potentiate certain active ones and offer combinations with each other numbering in the thousands—presenting a complexity that makes it virtually impossible for microbes to work around.

Garlic is one example, as discussed above. For a long time, many people thought there was only one "active" component in garlic, allicin. It was believed that raw garlic had very little biological activity, but that when a person would "damage" garlic cloves—by slicing, cooking, or chewing them—the enzyme alliinase would immediately convert non-active alliin into the active ingredient, allicin. However, researchers now know that allicin is rapidly oxidized. In the process of oxidation, allicin breaks down into more than 100 biologically active sulfur-containing compounds. While allicin may still serve as a general marker of garlic's potency, research increasingly points to S-allylcysteine and other bioactive compounds as the most therapeutically active ingredients in garlic. This means that the single natural ingredient, garlic, offers many thousands of different combinations of biochemicals that can defend against invading pathogens with no possibility that the pathogens can mutate around them.

The formula for finding the number of combinations of k (n_C_k) objects you can choose from a set of n objects is:

$$n\_C\_k = \frac{n!}{k!(n-k)!}$$

With 100 objects/compounds to work with and possible combinations ranging from any 2 of them to any 99 of them, as is found in just garlic, the complexity is statistically too much for simple pathogens to evolve around. And then when you combine several natural substances in one formula, as in the present description, the combinations of compounds is beyond counting. Without intending to be bound by theory, it is believed that microbes cannot evolve around the homeopathic and/or herbal or nutraceutical combinations as described herein and thus do not develop resistance.

Another embodiment includes combining certain formulations with fruit or vegetable juices in single shot servings for taste and convenience.

Additional ingredients that could be used in a nutritional or medicinal formulation include the following.

*Gelsemium*. Along with *Bryonia*, *Gelsemium* was one of the primary homeopathic remedies used to treat the 1918 Spanish Flu. The homeopathic remedy gelsemium is prepared using the freshly obtained roots of the twisting yellow jessamine (*Gelsemium sempervirens*) vine belonging to the Gelsemiaceae family and is used to treat pain and respiratory problems. This homeopathic remedy is also prescribed to treat health conditions, such as severe influenza or throbbing throats accompanied with headaches with double vision, feebleness, wilted limbs, fever, colds as well as intense and tired out eyelids. It is reported that homeopathy was 98% successful in treating the Spanish flu epidemic in 1918. According to Dr. Frank Wieland, MD, in Chicago, "(With) 8,000 workers we had only one death. Gelsemium was practically the only remedy used. We used no aspirin and no vaccines." Ohio reported that 24,000 cases of Spanish flu treated allopathically had a mortality rate of 28.2% while 26,000 cases of flu treated homeopathically had a mortality rate of 1.05%. In Connecticut, 6,602 cases were reported, with 55 deaths, less than 1%. Dr. Roberts, a physician on a troop ship during WWI, had 81 cases of flu on the way over to Europe. He reported, "All recovered and were landed. Every man received homeopathic treatment." ("Homeopathy in Influenza—a Chorus of Fifty in Harmony," by W. A. Dewey, MD., University of Michigan. *The Journal of the American Institute of Homeopathy*, May 1921, pp. 1308-1043).

*Arnica* can help when flu is accompanied by a feeling of soreness, as if bruised internally and externally. It is also helpful for high fever, dry cough, sore throat, croupy cough, and pneumonia.

*Baptisia* is useful when the flu is accompanied by high fever and there is profuse sweating and intense thirst.

*Eupatorium perfoliatum* is used when the flu is accompanied by body pains so severe, that the bones feel broken. It is also invaluable when troubled by high fever and intense chills.

Nux Vomica helps when there is shivering and high sensitivity to light, noise and odors.

Phosphorus is used when the flu affects the lungs, with heavy coughing and blood in the sputum.

Camphora is prescribed when the flu is associated with laborious, asthmatic breathing, accumulation of phlegm in the air tubes, and cold, dry skin.

Elder (*Sambucus nigra*), or elderberry extract, has a tradition of use for the treatment of colds and flu and has stood the test of science. The flowers from this plant have demonstrated antiviral activity against both influenza types A and B, as well as herpes simplex virus type 1. It also possesses anti-inflammatory activity. A clinical study showed that a standardized elderberry extract, Sambucol, improved the symptoms of influenza with a complete recovery in two to three days, compared to a six-day recovery period for the group not receiving the herb. In this study, patients were diagnosed with influenza type B. (*The Journal of International Medical Research* (2004) 32 (2): 132-40). Elder may act by stimulating the body's own interferon or by preventing attachment of the virus to the body's surfaces. See also, *Eur. Cytokine Netw.* (2001) 12(2):290-6.

Licorice root has also demonstrated antiviral activity. When mice infected with lethal doses of influenza virus were treated with glycyrrhizin, an active component of licorice, they were protected from death due to the virus and had less lung damage than did mice treated with saline controls (*Antimicrobial Agents and Chemotherapy* (1997) Vol. 41(3), 551-556).

The common cold (also known as nasopharyngitis, rhinopharyngitis, acute coryza, or simply a "cold") is a viral infectious disease of the upper respiratory system which affects primarily the nose. Symptoms include a cough, sore throat, runny nose, and fever which usually resolve in seven to ten days, with some symptoms lasting up to three weeks. Well over 200 viruses are implicated in the cause of the common cold; the rhinoviruses are the most common.

The typical symptoms of a cold include cough, runny nose, nasal congestion and a sore throat, sometimes accompanied by muscle ache, fatigue, headache, and loss of appetite.

A cold usually begins with fatigue, a feeling of being chilled, sneezing, and/or a headache, followed in a couple of days by a runny nose and cough. Symptoms typically peak two to three days after infection onset, and usually resolve in seven to ten days but some can last for up to three weeks.

Studies suggest that Zinc, if taken within 24 hours of the onset of symptoms, reduces the duration and severity of the common cold in healthy people.

The nutraceutical compositions disclosed herein may be administered in combination with a nutraceutically acceptable carrier. The active ingredients in such formulations may comprise from 1% by weight to 99% by weight, or alternatively, 0.1% by weight to 99.9% by weight. "Nutraceutically acceptable carrier" means any carrier, diluent or excipient that is compatible with the other ingredients of the formulation and not deleterious to the user.

Delivery System

Suitable methods of administration include, but are not limited to, sublingual, buccal, oral, and the like.

Suitable dosage forms include tablets, capsules, solutions, suspensions, powders, gums, and confectionaries. Other sublingual delivery systems include, but are not limited to, dissolvable tabs under and on the tongue, liquid drops, and beverages. Edible films, hydrophilic polymers, oral dissolvable films or oral dissolvable strips can be used.

Liquid-based nutritional or dietary supplement compositions for oral administration can be prepared in water, juices, or other aqueous vehicles. Useful liquid forms include solutions, suspensions, emulsions, and the like. Microemulsions and microencapsulations are contemplated. In addition to the above enumerated ingredients or compounds, liquid nutritional compositions can include suspending agents such as, for example, methylcellulose, alginates, tragacanth, pectin, kelgin, carrageenan, acacia, polyvinylpyrrolidone, polyvinyl alcohol, and the like. The liquid nutritional or dietary supplement compositions can be in the form of a solution, emulsion, syrup, gel, or elixir including or containing, together with the above enumerated ingredients or compounds, wetting agents, surfactants, dispersants, emulsifiers, sweeteners, and coloring and flavoring agents. Various liquid and powder nutritional compositions can be prepared by conventional methods.

The nutritional and dietary supplement compositions may or may not be presented in unit dosage forms and/or servings, depending on the delivery system and/or the end user. Unit dosage, for example, would be applicable to a ready-to-drink (RTD) delivery system. In such form, the preparation is subdivided into unit doses containing appropriate quantities of the nutritional or active component(s). The unit dosage form can be a packaged preparation, the package containing discrete quantities of preparation.

Solid nutritional compositions for oral administration in connection with a method for preventing or treating colds and/or flu may optionally contain, in addition to the above enumerated nutritional composition ingredients or compounds: carrier materials such as corn starch, gelatin, acacia, microcrystalline cellulose, kaolin, dicalcium phosphate, calcium carbonate, sodium chloride, alginic acid, and the like; disintegrators including microcrystalline cellulose, alginic acid, and the like; binders including acacia, methylcellulose, sodium carboxymethylcellulose, polyvinylpyrrolidone, hydroxypropyl methylcellulose, ethyl cellulose, and the like; and lubricants such as magnesium stearate, stearic acid, silicone fluid, talc, waxes, oils, colloidal silica, and the like. For example, the active agent may be combined with at least one excipient such as fillers, binders, humectants, disintegrating agents, solution retarders, absorption accelerators, wetting agents, surfactants, dispersants, emulsifiers, absorbents, or lubricating agents. Other useful excipients include magnesium stearate, calcium stearate, mannitol, xylitol, sweeteners, starch, carboxymethylcellulose, microcrystalline cellulose, silica, gelatin, silicon dioxide, and the like. The usefulness of such excipients is well known in the art.

In one embodiment, the nutritional composition may be in the form of a liquid. In accordance with this embodiment, a method of making a liquid composition is provided.

Liquid nutritional compositions for oral administration in connection with a method for preventing or treating colds and/or flu can be prepared in water or other aqueous vehicles. In addition to the above enumerated ingredients or compounds, liquid nutritional compositions can include suspending agents such as, for example, methylcellulose, alginates, tragacanth, pectin, kelgin, carrageenan, acacia, polyvinylpyrrolidone, polyvinyl alcohol, and the like. The liquid nutritional compositions can be in the form of a solution, emulsion, syrup, gel, or elixir including or containing, together with the above enumerated ingredients or compounds, wetting agents, sweeteners, and coloring and flavoring agents. Various liquid and powder nutritional compositions can be prepared by conventional methods. Various ready-to-drink formulations (RTD's) are contemplated.

The embodiments described herein can be assembled from liquids obtained through several separate processes, including, but not limited to, homeopathic, pressings, and extracts.

Homeopathic remedies are made from natural components—mineral, animal, and plant extracts are the base of these natural remedies which are then diluted through altering the degree of concentration to avoid creating side effects that can be disagreeable. Paradoxically, it is postulated that the more a homeopathic remedy is diluted, the more effectively a remedy will work.

There is a very distinct process for making homeopathic remedies. For example, when making a homeopathic remedy which is of plant or animal nature the extract or herb material, which generally includes a soluble substance or substances (or, alternatively, is admixed with another soluble substance), is dissolved in a mixture of alcohol (ethanol) and water (approximately ninety percent pure alcohol and ten percent distilled water, although the ratio can vary). This mixture is optionally set aside for two to four weeks. It is periodically shaken and then is press strained once it has cured. This formulation procedure yields a remedy referred to as a "mother tincture." See the references that follow, for example, regarding preparation of mother tinctures.

As used herein the terms "homeopathic" and "homeopathic ingredient" are defined in accordance with The Federal Food, Drug and Cosmetic Act (21 U.S.C. 351), which is incorporated herein by reference, and includes those agents or drugs used in the practice of homeopathy and listed in the Homeopathic Pharmacopeia of the United States (HPUS), the entirety of which is also incorporated herein by reference.

Also incorporated herein by reference are the following homeopathic texts: "Materia Medica with Repertory," $9^{th}$ Edition, by William Boericke, M.D. (Boericke & Tafel, Santa Rosa, Calif., 1927) and "A Dictionary of Practical Materia Medica," reprinted 2006, by John Henry Clarke, M.D. (B. Jain Publishers, New Delhi, 2006). Mother tincture examples (as in Clarke): *Bryonia alba* (white bryony) tincture of root procured before flowering, Vol. I, p. 310; *Pulsatilla* (windflower herb) tincture of entire fresh plant when in flower, Vol. II, p. 907; *Allium Cepa* (common red onion) tincture of the onion, or of the whole fresh plant, Vol. I, p. 53.

The mother tincture is diluted to produce different remedy potencies. To do this one may use one of two scales: the decimal (x or "X") and the centesimal (c or "C"). Optionally, an alcohol/water mixture is used for dilution in various stages.

Between each of the stages of dilution, the diluted tincture is optionally succussed (shaken vigorously). Also, the decimal scale dilution factor (X) is 1:10 and in the centesimal (C) it is 1:100.

*Bryonia alba* mother tincture is available from Vitality Works Inc., Albuquerque, N.M.

*Pulsatilla* mother tincture is available from Vitality Works Inc., Albuquerque, N.M.

*Allium cepa* mother tincture is available from Vitality Works Inc., Albuquerque, N.M.

For example: To produce a 1 C potency of the *Bryonia alba* remedy, one drop of the mother tincture is added to 99 drops of an alcohol/water mixture and succussed. To produce a 2 C potency, one drop of the 1 C mixture is added to 99 drops of an alcohol/water mixture and succussed. The number of a homeopathic remedy shows how many times it has been diluted and succussed, for example, *Bryonia* 6 C has been diluted and succussed six times. Standard dilutions include 6×, 12×, and 30×.

Without being bound by theory, it is noted that statistical and probability considerations may apply in a given solute/solution combination where dilutions reach or exceed 24× ($1/10^{24}$ dilution), in comparison with Avogadro's number. The embodiments as described are not intended to be limited merely by theoretical calculations, particularly where a statistical probability may apply.

Pressing is reserved for vegetable components such as, for example, garlic, onion, habanero, ginger, and horseradish. For example, the raw vegetable components may range from about 2 oz. by weight (avoirdupois) to about 16 oz. by weight (corresponding to a range from about 55 grams to about 454 grams). The process involves mechanically grinding an appropriate amount of the given vegetables into fine puree, and then using hydraulic presses to force the juice of the puree through a filtering medium until the desired volume(s) of purified juice is isolated. ACV may be optionally added to the purees or purified juices and may be used in the ratios described in Example 1. This liquid is then combined with the determined or calculated homeopathic component dilution. Useful commercial pressings of ginger, onion, garlic, horseradish, and habanero (optionally diluted in ACV) can be obtained from Western Mixers—Wholesale Organics (Los Angeles, Calif.).

Olive leaf extract can be made by grinding up the leaf into a fine powder and then suspending into a solution of alcohol and water. The solution is regularly agitated or pulverized (e.g., by ultrasonication) over time and then pressed through a filtering medium to extract the bio-active ingredients. Powdered olive leaf is available from Pacific Botanicals, Grants Pass, Oreg. Tinctures of this extract can be prepared in alcohol-based media or may be purchased from commercial sources.

Herbal extracts such as olive leaf extract, for example, can be made by grinding up the herbs into a fine powder, placing the powder (e.g., 1-4 oz. equiv. to about 28-113 g) into a jar, and adding a solution of alcohol and water (alcohol vol. can range from about 45-55% of the total volume) until the powder is completely covered. The solution is regularly agitated or pulverized (e.g., by ultrasonication) over time and then pressed through a filtering medium to extract the bio-active ingredients (e.g. about 6-12 fl. oz.), providing an olive leaf tincture. Dried herbs for making extracts are available from Pacific Botanicals, Grants Pass, Oreg.

Oil of mountain oregano can be produced in a yet another different way. The plant or plant parts can be ground up, cold pressed, and then steam distilled. The resultant extract is then emulsified in pure olive oil, which serves as the carrier. One useful oil of WM oregano extract is available as Oreganol (North American Herb and Spice, Buffalo Grove, Ill.).

*Bryonia alba* and *Pulsatilla* preparations can be manufactured as described above in a variety of dilutions.

EXAMPLE 1

In accordance with one embodiment:
Homeopathic components make up about 10% by volume of the formula—evenly divided between:
*Bryonia alba* 30×; prepared as described above using white bryony herb; and
*Pulsatilla* 30×; prepared as described above using windflower herb.
Traditional herbal and nutraceutical components (as described above) make up about 90% by volume as follows:

| | |
|---|---|
| Ginger juice pressing | 12 fl. oz. |
| Onion juice pressing | 16 fl. oz. |
| Garlic juice pressing | 12 fl. oz. |
| Olive leaf tincture | 12 fl. oz. |
| Horseradish juice pressing | 8 fl. oz. |
| Habañero juice pressing | 4 fl. oz. |
| Liquid ionic zinc (500 ppm) | 100 ml (approx. 3.4 fl. oz.) |
| Oil of WM oregano | 5 ml (approx. 0.2 fl. oz.) |
| Apple cider vinegar (ACV) | 72 fl. oz. |

EXAMPLE 1A

In accordance with Example 1, the homeopathic components are provided at dilutions 20×.

EXAMPLE 1B

In accordance with Example 1, the homeopathic components are provided at dilutions 10×.

EXAMPLE 1C

In accordance with Example 1, the homeopathic components are provided at dilutions 5×.

EXAMPLE 2

In accordance with another embodiment, a 3 ml serving of the embodiment as described in Example 1 can be blended with a 57 ml serving of tomato juice and portioned and packaged in a 2 fl. oz "plastic shot" container (i.e., ready-to-drink).

EXAMPLE 3

In accordance with a further embodiment, a 10 ml serving of the embodiment as described in Example 1 can be blended with a 230 ml serving of orange juice and portioned and packaged in an 8 fl. oz tetra pack container.

EXAMPLE 4

In order to determine pathogenic load or viral load several techniques may be used. Real-time reverse transcription PCR (RT-PCR) may be performed as described in singleplex or multiplex format (Watzinger, F., et al., "Real-Time Quantitative PCR Assays for Detection and Monitoring of Pathogenic Human Viruses in Immunosuppressed Pediatric Patients," *J. Clin. Microbiol.* (2004) 42(11): 5189-5198, and references cited therein; and Boivin, G., et al., "Multiplex Real-Time PCR Assay for Detection of Influenza and Human Respiratory Syncytial Viruses," (HRSV) *J. Clin. Microbiol.* (2004) 42(1): 45-51); or MassTag PCR analysis (Lamson, D., et al., "MassTag Polymerase-Chain-Reaction Detection of Respiratory Pathogens, Including a New Rhinovirus Genotype, That Caused Influenza-Like Illness in New York State during 2004-2005," *J. Infect. Dis.* (2006) 194: 1398-1402), each of the aforementioned references being incorporated herein by reference. As reported in Watzinger, et al., rapid antigen assays may also be suitable for viral detection (for example, influenza A and B (Directigen, Becton Dickison, Sparks, Md.), and HRSV (RSV TestPack, Abbott Laboratories, Abbott Park, Ill.). For example, the PAXgene Blood RNA Kit IVD (in vitro diagnostic) is available from Qiagen, Inc. USA (Valencia, Calif.), and may be used for isolation and purification of intracellular RNA from whole blood stabilized in PAXgene Blood RNA Tubes for IVD, followed by applying the known manual or automated RT-PCR technique, or other known PCR techniques, for viral gene expression and biomarker detection. Conventional virus culture may also be used.

EXAMPLE 4A

In accordance with an embodiment, a human individual afflicted with cold and/or flu symptoms is administered orally a serving as in Example 2. After about 24 to 48 hours, it is expected that the symptoms will be decreased in the individual.

EXAMPLE 4B

In accordance with another embodiment, a human individual afflicted with cold and/or flu symptoms is administered orally a serving as in Example 2. After about 24 to 48 hours, it is expected that the pathogenic load as measured by quantification of gene expression will be substantially decreased (compared to an initial measurement), or normalized.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

I claim:

1. A nutritional composition comprising at least one homeopathic component selected from the group consisting of *Bryonia alba* and *Pulsatilla* spp., in combination with at least one component selected from the group consisting of ginger, onion, garlic, olive leaf extract, horseradish, habanero, liquid ionic zinc, oil of wild mountain oregano, and apple cider vinegar, and a nutraceutically acceptable carrier.

2. The nutritional composition of claim 1, wherein the nutraceutically acceptable carrier is aqueous ethanol.

3. The nutritional composition of claim 1, further comprising an edible liquid in a ready-to-drink formulation.

4. The nutritional composition of claim 1, wherein the at least one homeopathic component is present in a 30× dilution.

5. The nutritional composition of claim 1, wherein the at least one homeopathic component is present in a dilution of from about 5× to about 20×.

6. A dietary supplement composition comprising at least one homeopathic component selected from the group consisting of *Bryonia alba* and *Pulsatilla* spp., in combination with one or more components selected from the group consisting of ginger, onion, garlic, olive leaf extract, horseradish, habanero, liquid ionic zinc, and oil of wild mountain oregano, and an edible liquid in a ready-to-drink (RTD) formulation.

7. The dietary supplement composition of claim 6, wherein the at least one homeopathic component is present in a 30× dilution.

8. The dietary supplement composition of claim 6, wherein he at least one homeopathic component is present in a dilution of from about 5× to about 20×.

9. The dietary supplement composition of claim 6, wherein the edible liquid is apple cider vinegar.

10. The dietary supplement composition of claim 9, wherein the one or more components selected from the group consisting of ginger, onion, garlic, olive leaf extract, horseradish, habanero, liquid ionic zinc, and oil of wild mountain oregano are prepared by pureeing, pressing, and diluting with apple cider vinegar.

* * * * *